United States Patent [19]
Tsuji

[11] Patent Number: 5,840,987
[45] Date of Patent: Nov. 24, 1998

[54] PROCESS FOR THE PREPARATION OF ETHYLAMINES

[75] Inventor: Yasuo Tsuji, Ohtake, Japan

[73] Assignee: Daicel Chemical Industries, Ltd., Sakai, Japan

[21] Appl. No.: 965,171

[22] Filed: Nov. 6, 1997

[30] Foreign Application Priority Data

Nov. 8, 1996 [JP] Japan .................................. 8-312873

[51] Int. Cl.⁶ .................................................. C07C 209/16
[52] U.S. Cl. ............................................................. 564/479
[58] Field of Search ............................................. 564/479

Primary Examiner—Brian M. Burn
Attorney, Agent, or Firm—Morgan & Finnegan, LLP

[57] ABSTRACT

Disclosed is a process for the preparation of a process for the separation and purification of amines from a mixed reaction crude liquid containing ethylamines prepared by a reaction of ethylalcohol or acetaldehyde with ammonia, and triethylamine can be predominantly prepared without accumulation of ingredients having intermediate boiling-points.

2 Claims, 1 Drawing Sheet

PROCESS FOR THE PREPARATION OF ETHYLAMINES

FIELD OF THE INVENTION

The present invention relates to a process for the separation and purification of amines from a mixed reaction crude liquid containing ethylamines prepared by a reaction of ethylalcohol or acetaldehyde with ammonia.

BACKGROUND OF THE INVENTION

As processes for the preparation of ethylamines such as monoethylamine, diethylamine, and triethylamine, there are known an aldehyde process in which acetaldehyde is allowed to react with ammonia and hydrogen using a catalyst, and an ethylalcohol process in which ethylalcohol is allowed to react with ammonia and hydrogen using a catalyst. It is looked upon that steps for the purification of the amines in the processes are intrinsically identical to each other. In the steps for the purification of the amines, there has been usually carried out a separation of a mixture containing water, ethylalcohol, and triethylamine after removal of ammonia, monoethylamine, and diethylamine from a mixed reaction crude liquid, as shown by solid lines in FIG. 1.

A feeding liquid which is the mixture containing water, ethylalcohol, and triethylamine is fed into a first distillation column through the line A, ethylalcohol is discharged (the line E) from a bottom of the distillation column together with water, and triethylamine and partial ethylalcohol are distilled out of a top of the distillation column through the line B by azeotropic distillation with water. Distillate is transferred to a decanter, and an upper layer liquid (a triethylamine rich layer) is separated from a lower layer liquid (a water layer) therein.

The upper layer liquid in the decanter is fed into a second distillation column through the line D, and a crude triethylamine can be obtained through the line G from a bottom of the second distillation column.

Water and ethylalcohol dissolved in the upper layer liquid in the decanter are distilled toward a top of the second distillation column, and those are recirculated into the decanter through the line F, whereby, those are prevented to mix with the crude triethylamine together with other ingredients having intermediate boiling-points.

If the crude triethylamine obtained in the line G has a high purity, it is obtained as a product. Further, in the case that it contains a large amount of impurities having high-boiling-points, it is obtained as a product by removing the impurities having high-boiling-points. As a method for removing the impurities having high-boiling-points, there is a process that vapor is discharged by a side streaming from a position in the vicinity of a bottom in the second distillation column.

For example, JP-B-76026535 Official Gazette states that an upper layer liquid obtained in a decanter is distilled to obtain triethylamine as a product in a bottom of a distillation column, and a product in a top of the distillation column is recirculated into the decanter.

Further, JP-B-90034937 Official Gazette is characterized in that a triethylamine-rich extract is obtained by a multi-stage liquid-liquid extraction of a mixture composed of triethylamine, diethylamine, ethylalcohol, and water.

However, in descriptions of embodiments, the triethylamine-rich extract is manufactured as a product by a side stream in distillation, and a distillate in a top of column is recirculated into an extractor.

As described hereinabove, although compounds having boiling points between diethylamine and triethylamine are partially discharged from the bottom of the first distillation column, the greater part thereof has been accumulated in the upper layer liquid of the decanter. The compounds having boiling points between diethylamine and triethylamine are by-produced in the reactions, and since the amount of by-products is usually small, for example, in the case that triethylamine is produced in a small amount and in the case that triethylamine is produced within a short time of period, problems are not caused because of a low concentration of accumulation in a decanter.

However, in view of a rapid increase in recent demand of triethylamine, it has been requested that triethylamine is predominantly produced in the preparation of the amines.

In the case that triethylamine is predominantly produced in the preparation of the amines, there becomes high the concentration of accumulation in ingredients having boiling points between diethylamine and triethylamine, whereby, inferiority in liquids-separation is finally caused in decanter, or impurities accumulated in the decanter are mixed into a liquid in a bottom of the second distillation column before causing the inferiority of liquids-separation, resulting in that the impurities are occasionally mingled into triethylamine.

The present invention aims at preventing an increase of the concentration of accumulation in ingredients having boiling points between diethylamine and triethylamine in a decanter in a step of separating triethylamine in the process for the preparation of ethylamines.

SUMMARY OF THE INVENTION

An aspect of the present invention relates to a process for the preparation of ethylamines in which respective amines are separated from a mixed reaction crude liquid containing water, ammonia, ethylalcohol, monoethylamine, diethylamine, and triethylamine obtained by a reaction of ethanol with ammonia under a hydrogen atmosphere using a catalyst, the improvement which comprises the steps; distilling a mixture containing water, ethylalcohol, and triethylamine in a first distillation column after removing ammonia, monoethylamine, and diethylamine from said mixed reaction crude liquid, discharging ethylalcohol and water from a bottom of the distillation column, separating a distillate containing water, triethylamine, and partial ethylalcohol distilled out of a top of the distillation column into an upper layer liquid and a lower layer liquid in a decanter, recirculating said lower layer liquid into the first distillation column, distilling out said upper layer liquid in a second distillation column and recirculating a distillate from a top of the second distillation column into the decanter, obtaining ethylamine from a bottom of the second distillation column, and partially recirculating the upper layer liquid into a reaction system between ethylalcohol and ammonia.

According to the aspect of the present invention, triethylamine can be predominantly prepared without accumulation of ingredients having intermediate boiling-points. The upper layer liquid in the decanter has not been discharged in conventional processes.

DETAILED DESCRIPTION OF THE INVENTION

Figure 1:
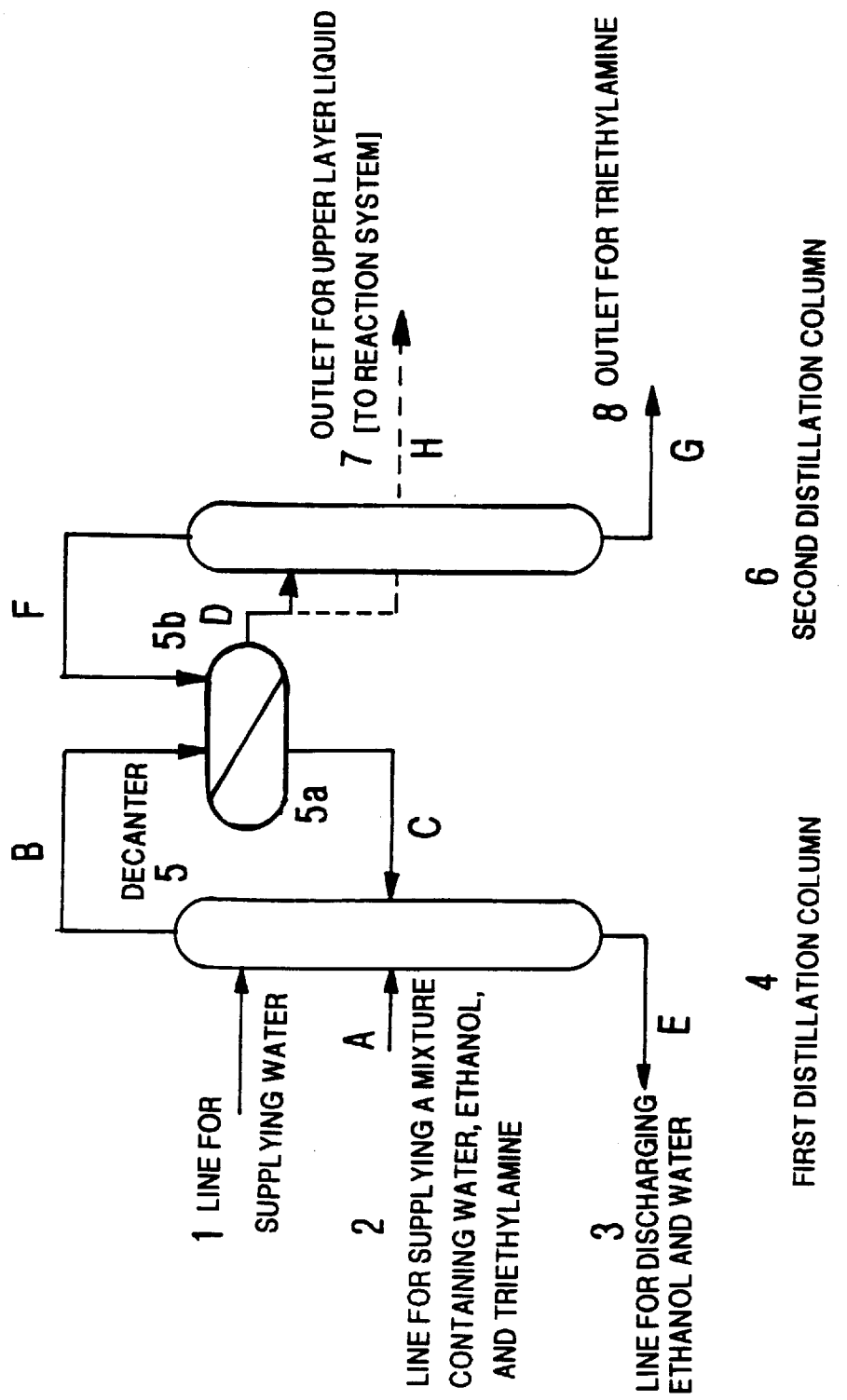
FIG. 1 is a flow sheet of a process for the separation and purification of ethylamines in the present invention. The dotted line H shows a discharging line of the upper layer liquid in the decanter.

According to a first aspect of the present invention, there is provided a process for the preparation of ethylamines in which respective amines are separated from a mixed reaction crude liquid containing water, ammonia, ethylalcohol, monoethylamine, diethylamine, and triethylamine obtained by a reaction of ethylalcohol with ammonia under a hydrogen atmosphere using a catalyst, the improvement which comprises the steps; distilling a mixture containing water, ethylalcohol, and triethylamine in a first distillation column after removing ammonia, monoethylamine, and diethylamine from said mixed reaction crude liquid, discharging ethylalcohol and water from a bottom of the distillation column, separating a distillate containing water, triethylamine, and partial ethylalcohol distilled out of a top of the distillation column into an upper layer liquid and a lower layer liquid in a decanter, recirculating said lower layer liquid into the first distillation column, distilling out said upper layer liquid in a second distillation column and recirculating a distillate from a top of the second distillation column into the decanter, obtaining ethylamine from a bottom of the second distillation column, and partially recirculating the upper layer liquid into a reaction system between ethylalcohol and ammonia.

The ingredients accumulated in a decanter are basically compounds having boiling points between diethylamine and triethylamine, as a result of an analysis for the ingredients by the present inventor, it was found out that the compounds mainly include n-butyl amine, secondary butyl amine, and N-ethylisopropylamine, etc. Further, it was identified that the compounds are converted into compounds having higher boiling points such as ethylbutyl amine, diethylbutyl amine, ethylsecondarybutyl amine, and diethylisopropyl amine, etc. by recirculating the upper layer liquid in the decanter into a reaction system.

The present invention was completed by the finding that higher amination or amine-converting reaction is caused by recirculating the compounds having intermediate boiling points accumulated in a decanter into the reaction system, and the compounds are converted into compounds having higher boiling points.

In the following, the present invention will be specifically described based on the FIG. 1 which only shows an outline of main equipments.

A feeding liquid containing water, triethylamine, partial ethylalcohol, and a minor amount of by-products, in which ammonia, monoethylamine, and diethylamine are separated from a reaction crude liquid obtained in a reaction system (not shown in the FIG. 1), is fed into the first distillation column 4 for removing ethylalcohol through the feeding line A. A minor amount of the by-products mainly contain compounds such as n-butyl amine, secondary butyl amine, and N-ethylisopropylamine, ethylbutyl amine, diethylbutyl amine, ethylsecondarybutyl amine, and diethylisopropyl amine, etc.

The first distillation column 4 is usually operated in an ordinary pressure and a column-top temperature ranging from 70° to 80° C. and a column-bottom temperature ranging from 95° to 105° C., and a nearly whole amount of ethylalcohol is discharged together with water from the column-bottom through the line E by distilling while extracting with water charged from the column-top. At that time, the by-products brought in from the line A are partially discharged from the column-bottom. Ethylalcohol is recollected in a succeeding distillation column (not shown in the FIG. 1) from an ethylalcohol aqueous solution discharged from the column-bottom, and the recollected ethylalcohol is recirculated into the reaction system.

A distillate in a column-top of the first distillation column 4 is fed into the decanter 5 through the line B. The distillate contains water, triethylamine, a small amount of ethylalcohol, and a residual part of the by-products.

In the first distillation column 4, in the case that the amount of water to be fed at the column-top is small, since extracting efficiency becomes worse, there decreases ethylalcohol discharged from a column-bottom, resulting in that liquids-separability in the decanter 5 becomes worse by accumulation in the decanter 5. Accordingly, although it becomes necessary to feed water exceeding a certain amount, a too larger feeding amount requires a large amount of steam for heating in the first distillation column 4, and the amount-of steam also increases in a distillation column for recollecting ethylalcohol from a column-bottom liquid in a succeeding step, resulting in that it is not economical because of becoming worse in utility.

Accordingly, the amount of water to be fed at the column-top in the first distillation column 4 is approximately 0.3–1.0 times (by weight) based on the amount of the liquid to be fed into the first distillation column 4, which contains water, ethylalcohol, triethylamine, and a minor amount of the by-products.

In the decanter 5, the upper layer liquid 5b (a triethylamine layer) is separated from the lower layer liquid 5a (a water layer). The decanter 5 is usually operated in an ordinary pressure and at a temperature of 50°–90° C., and preferably 60°–75° C. Since triethylamine and water are dissolved into each other at not more than approximately 20° C., the decanter 5 is stably operated while maintaining at relatively high temperatures in order to maintain liquids-separability. The lower layer liquid 5a in the decanter 5 is fed into the first distillation column 4 to distill through the line C, which is composed of a small amount of triethylamine and ethylalcohol, a minor amount of by-products, and a large amount of water. The upper layer liquid 5b in the decanter 5 is fed into the second distillation column 6 through the line D.

The upper layer liquid 5b in the decanter 5 is composed of a small amount of water, a small amount of ethylalcohol, a residual amount of the by-products, and triethylamine. Since the by-products are distributed in a large amount into the upper layer liquid 5a in the decanter 5, the large part results in being fed into the second distillation column 6 through the line D.

The second distillation column 6 is also usually operated in an ordinary pressure and at a column-top temperature of 80°–90° C., and a column-bottom temperature of 90°–100° C. The second distillation column 6 is equipped for the purpose of separating water and ethylalcohol from triethylamine.

Toward the column-top, triethylamine is distilled together with water, ethylalcohol, and the by-products, and it is fed into the decanter 5 through a condenser (not shown in the FIG. 1) in the line F. From the column-bottom, there are discharged a minor amount of water, a minor amount of ethylalcohol, and a minor amount of the by-products, and triethylamine through the line G.

The second distillation column 6 must be operated so that water, ethylalcohol, and ingredients accumulated in the decanter 5 are not fallen toward the column-bottom as far as possible. For that reason, the second distillation column 6 is operated while controlling the amount to be distilled.

However, in the case that the upper layer liquid 5b in the decanter is not discharged (the line H), the by-products become accumulated in the decanter. Elevation in the concentration of accumulated substances finally causes elevation in the concentration of the by-products which are discharged together with triethylamine from the bottom of the second distillation column 6. In an extent of concentration range, although an operation can be carried out in which the by-products are not fallen toward the bottom of the column by increasing the amount to be distilled in the second distillation column 6 under the expense of an efficiency in utility, since the accumulation of the by-products does not become absolutely zero, the by-products are finally mingled in triethylamine in a high concentration.

On the other hand, as shown by the dotted line H in the present invention, in the case that the upper layer liquid 5b in the decanter 5 which is rich in triethylamine is partially recirculated into a reaction system, the by-products which are ingredients having intermediate boiling points are converted into compounds having higher boiling points in a reaction vessel, whereby, the accumulation can be prevented in the decanter 5.

The amount of the upper layer liquid 5b in the decanter to be discharged from the line H is controlled while watching temperatures in the first distillation column 4.

In the case that the amount to be discharged is slight, temperature decline in the first distillation column 5 by the accumulation of the by-products, that is, there is caused an increase in the concentration of the by-products in triethylamine from the line G. In the case that the upper layer liquid 5b is excessively discharged, since there increases a feeding amount into the reaction system, it causes an increase of capacity in the reaction vessel, and an increase in use of utility, resulting in an economical loss. Usually, the amount to be discharged is preferably approximately 10–20% based on the weight of the recirculating amount into the second distillation column 6. If a distillation column for removing low-boiling-point-ingredients is equipped in a succeeding step of the second distillation column 6, through which a crude triethylamine is refined, a triethylamine product having high purity can be obtained regardless of the concentration of the by-products in the crude triethylamine. However, a plant cost unavoidably rises. On the other hand, in the present invention, since ingredients having low-boiling-points in triethylamine can be removed by only partially recirculating the upper layer liquid 5b in the decanter, there is not required the distillation column for removing the ingredients having low-boiling-points in a succeeding step.

Accordingly, economical merit is large.

Further, also in an aldehyde process for the preparation of ethylamines in which acetaldehyde is employed in place of ethylalcohol, there are produced ethylamines which are products and by-products which are ingredients having intermediate boiling-points as well as in the ethylalcohol process. All amount of acetaldehyde is allowed to react, and ethylalcohol is produced as a by-product.

Accordingly, a preparation apparatus and a method for separating amines in the above-mentioned alcohol process can be applied also in the aldehyde process.

Hereinafter, although the present invention is more specifically illustrated by Examples, the present invention is not limited by the Examples.

EXAMPLE 1

Operations were carried out according to the FIG. 1.

Feeding liquid A was fed into the first distillation column 4, which was obtained by removing ammonia, monoethylamine, and diethylamine from a crude reaction liquid prepared by feeding ethylalcohol which is a raw material in feeding rate of 180 g/hour. The feeding liquid A contains triethylamine (36.5% by weight), ethylalcohol (13.8% by weight), and water (49.7% by weight), and feeding rate is 260 g/hour. In order to remove ethylalcohol in the first distillation column 4, an operation was carried out by feeding water from a column-top in feeding rate of 650 g/hour. A mixture was discharged through the line E from a bottom of the first distillation column 4, which contains ethylalcohol (4.4% by weight) and water (95.5% by weight) in discharging rate of 815 g/hour.

Upper layer liquid 5b in the decanter 5 was discharged through the lines D and H in discharging rate of 20 g/hour, and operation was carried out while recirculating the liquid 5b into a reaction system.

A mixture composed of triethylamine (99.9% by weight), and water (0.04% by weight) was discharged through the line G from a bottom of the second distillation column 6 in discharging rate of 75.5 g/hour.

Operations were continued for 7 days while monitoring a concentration change of a minor amount of by-products in the upper layer liquid 5b of the decanter 5, and analytical results are shown in Table 1. It is identified that the concentration of the by-products in the decanter 5 is not changed, and accumulation of the by-products is suppressed.

TABLE 1

| By-products | 1st day (wt %) | 3rd day (wt %) | 7th day (wt %) |
| --- | --- | --- | --- |
| A | 0.43 | 0.52 | 0.45 |
| B | 0.02 | 0.02 | 0.03 |
| C | 0.04 | 0.03 | 0.03 |
| D | 0.07 | 0.08 | 0.07 |
| E | 0.01 | 0.02 | 0.01 |
| F | 0.02 | 0.03 | 0.03 |

Comparative Example 1

Same procedures as described in Example 1 were followed except that the upper layer liquid 5b was not discharged from the decanter through the line H.

There was analyzed the concentration change of the by-products in the upper layer liquid 5b of the decanter, and analytical results are shown in Table 2.

It is identified that the concentration gradually elevates compared to the Example 1.

TABLE 2

| By-products | 1st day (wt %) | 3rd day (wt %) | 7th day (wt %) |
| --- | --- | --- | --- |
| A | 0.76 | 2.67 | 3.86 |
| B | 0.03 | 0.08 | 0.15 |
| C | 0.06 | 0.15 | 0.20 |
| D | 0.01 | 0.01 | 0.01 |
| E | ND | ND | ND |
| F | ND | ND | ND |

By-products are those in the upper layer liquid 5b of the decanter, and alphabets are as follows in the Tables 1 and 2.

A: N-ethylisopropyl amine
B: secondary butyl amine
C: n-butyl amine
D: diethylisopropyl amine
E: ethylsecondarybutyl amine
F: diethylbutyl amine While the invention has been described in detail and with reference to specific embodiments thereof, it will be apparent to one skilled in the art that various changes and modifications can be made therein without departing from the spirit and scope thereof.

What is claimed is:

1. In a process for the preparation of ethylamines in which respective amines are separated from a mixed reaction crude liquid containing water, ammonia, ethylalcohol, monoethylamine, diethylamine, and triethylamine obtained by a reaction of ethylalcohol with ammonia under a hydrogen atmosphere using a catalyst, the improvement which comprises the steps; distilling a mixture containing water, ethylalcohol, and triethylamine in a first distillation column after removing ammonia, monoethylamine, and diethylamine from said mixed reaction crude liquid, discharging ethylalcohol and water from a bottom of the distillation column, separating a distillate containing water, triethylamine, and partial ethylalcohol distilled out of a top of the distillation column into an upper layer liquid and a lower layer liquid in a decanter, recirculating said lower layer liquid into the first distillation column, distilling out said upper layer liquid in a second distillation column and recirculating a distillate from a top of the second distillation column into the decanter, obtaining ethylamine from a bottom of the second distillation column, and partially recirculating the upper layer liquid into a reaction system between ethylalcohol and ammonia.

2. A process for the preparation of ethylamines as set forth in claim 1, wherein acetaldehyde is employed in place of said ethylalcohol.

* * * * *